(12) United States Patent
Schindler et al.

(10) Patent No.: US 11,326,800 B2
(45) Date of Patent: May 10, 2022

(54) APPARATUSES AND METHODS FOR AIR QUALITY MAINTENANCE BY VENTILATION BASED ON POLLUTANT FORECAST

(71) Applicant: Honeywell International Inc., Morris Plains, NJ (US)

(72) Inventors: Zdeněk Schindler, Prague (CZ); Jakub Malaník, Prague (CZ); Tomáš Tvrdoň, Březina (CZ)

(73) Assignee: HONEYWELL INTERNATIONAL INC., Morris Plains, NJ (US)

( * ) Notice: Subject to any disclaimer, the term of this patent is extended or adjusted under 35 U.S.C. 154(b) by 163 days.

(21) Appl. No.: 16/655,820

(22) Filed: Oct. 17, 2019

(65) Prior Publication Data
US 2021/0116143 A1    Apr. 22, 2021

(51) Int. Cl.
| | | |
|---|---|---|
| *F24F 11/64* | (2018.01) | |
| *F24F 11/00* | (2018.01) | |
| *G01N 33/00* | (2006.01) | |
| *F24F 110/50* | (2018.01) | |

(52) U.S. Cl.
CPC .......... *F24F 11/64* (2018.01); *F24F 11/0001* (2013.01); *G01N 33/0004* (2013.01); *F24F 2110/50* (2018.01)

(58) Field of Classification Search
None
See application file for complete search history.

(56) References Cited

U.S. PATENT DOCUMENTS

| | | | | |
|---|---|---|---|---|
| 9,182,751 | B1* | 11/2015 | Reeder | G01N 33/004 |
| 2013/0211599 | A1* | 8/2013 | Yachiku | G05B 19/02 |
| | | | | 700/275 |
| 2016/0318368 | A1* | 11/2016 | Alger | G01C 21/3453 |
| 2017/0140282 | A1* | 5/2017 | Bai | G06N 7/00 |
| 2017/0184561 | A1 | 6/2017 | Bai et al. | |
| 2018/0039718 | A1* | 2/2018 | Bai | G06F 30/20 |
| 2018/0318746 | A1 | 11/2018 | Thomas | |
| 2019/0264940 | A1* | 8/2019 | Lee | F24F 11/30 |

OTHER PUBLICATIONS

Fang et al. 'AirSense: An Intelligent Home-based Sensing System for Indoor Air Quality Analytics' UBICOMP '16, Sep. 12-16, 2016.*
Xiahou et al. 'Indoor Air Monitoring System Based on Internet of Things and Its Prediction Model', Proceedings of ACM ICNSER conference (ICNSER'19), Mar. 15-16, 2019.*

(Continued)

*Primary Examiner* — Bernard G Lindsay
(74) *Attorney, Agent, or Firm* — Alston & Bird LLP

(57) ABSTRACT

Methods, apparatuses, and computer program products are disclosed for performing air quality maintenance. An example method include receiving an air quality dataset and generating a quality tendency projection based upon the air quality dataset that includes a quality rate of change. In an instance in which the quality tendency projection exceeds a prediction threshold and the quality rate of change exceeds a pollutant rate increase threshold, the method performs performing air degradation analysis. In an instance in which the quality tendency projection exceeds a warning threshold and the quality rate of change exceeds a pollutant rate decrease threshold, the method performs ventilation analysis.

20 Claims, 8 Drawing Sheets

(56) References Cited

OTHER PUBLICATIONS

Li et al. 'Indoor Air Quality Control of HVAC System' Proceedings of the 2010 International Conference on Modelling, Identification and Control, Okayama, Japan, Jul. 17-19, 2010.*
Wang et al. 'Intelligent Control of Ventilation System for Energy-Efficient Buildings With CO2 Predictive Model' IEEE Transactions on Smart Grid, vol. 4, No. 2, Jun. 2013.*
European search opinion dated Feb. 2, 2021 for EP Application No. 20191008.0, 2 pages.
European search report dated Feb. 2, 2021 for EP Application No. 20191008.0, 2 pages.

* cited by examiner

APPARATUSES AND METHODS FOR AIR QUALITY MAINTENANCE BY VENTILATION BASED ON POLLUTANT FORECAST

TECHNOLOGICAL FIELD

Example embodiments of the present invention relate generally to air quality monitoring and, more particularly, to reducing air pollutants.

GOVERNMENTAL RIGHTS

The project leading to this application has received funding from the European Union's Horizon 2020 research and innovation programme under grant agreement No 680517.

BACKGROUND

The air quality in open environments may be maintained by the nature of the space (e.g., outdoor location, fauna, and the like). In contrast, the interiors of buildings such as schools, commercial buildings, governmental buildings, or the like are often closed environments. As such, the quality of the air in these closed environments may be affected by the size of the interior, the number of people within the interior, ventilation, and any airflow within the interior.

BRIEF SUMMARY

Systems, apparatuses, methods, and computer program products are disclosed herein for performing air quality maintenance. In one embodiment, with reference to the claimed computed implemented method, a method for performing air quality maintenance may include receiving an air quality dataset that includes pollutant concentration data associated with respective time data. The method may further include generating a quality tendency projection based upon the air quality dataset that includes a quality rate of change. In an instance in which the quality tendency projection exceeds a prediction threshold and the quality rate of change exceeds a pollutant rate increase threshold, the method may include performing air degradation analysis. The air degradation analysis may include generating a pollutant increase forecast, and determining a critical time based upon the pollutant increase forecast. The critical time may include a time in which pollutant concentration is projected to exceed a critical threshold. In an instance in which the quality rate of change exceeds a pollutant rate decrease threshold, the method includes performing ventilation analysis. The ventilation analysis may include generating a pollutant decrease forecast, and determining a safe time based upon the pollutant decrease forecast. The safe time may include a time in which the pollutant concentration is projected to satisfy a safety threshold.

In some embodiments, in an instance in which the quality tendency projection exceeds the warning threshold, the method may include generating a warning transmission. In other embodiments, in an instance in which at least one pollutant concentration data entry exceeds the warning threshold, the method may include generating a warning transmission.

In some embodiments, performing the degradation analysis further includes receiving pollutant concentration data over a first time period from the air quality dataset. In such an embodiment, the method may further include selecting a parametric function that models the pollutant concentration data over the first time period and forecasting the parametric function (e.g., forecasting using the parametric function) over a second time period to generate the pollutant increase forecast.

In some embodiments, performing the ventilation analysis further includes receiving pollutant concentration data over a third time period from the air quality dataset. In such an embodiment, the method may include selecting a parametric function that models the pollutant concentration data over the first time period and forecasting the parametric function (e.g., forecasting using the parametric function) over a fourth time period to generate the pollutant decrease forecast.

In response to determining the critical time, the method may further include generating a regression ventilation model based upon the air quality dataset. In such an embodiment, the method may include determining a ventilation duration based upon the regression ventilation model. The ventilation duration may include a time required to reduce the pollutant concentration to satisfy the safety threshold.

In any embodiment, the critical threshold may be greater the prediction threshold, the prediction threshold may be greater than the warning threshold, and the warning threshold may be greater than the safety threshold. In some embodiments, the prediction threshold may be less than the warning threshold such as in instances in which a rapid increase of pollutants are provided to a relatively pollutant free environment.

The above summary is provided merely for purposes of summarizing some example embodiments to provide a basic understanding of some aspects of the invention. Accordingly, it will be appreciated that the above-described embodiments are merely examples and should not be construed to narrow the scope or spirit of the invention in any way. It will be appreciated that the scope of the invention encompasses many potential embodiments in addition to those here summarized, some of which will be further described below.

BRIEF DESCRIPTION OF THE DRAWINGS

Having described certain example embodiments of the present disclosure in general terms above, reference will now be made to the accompanying drawings. The components illustrated in the figures may or may not be present in certain embodiments described herein. Some embodiments may include fewer (or more) components than those shown in the figures.

DETAILED DESCRIPTION

Figure 1:
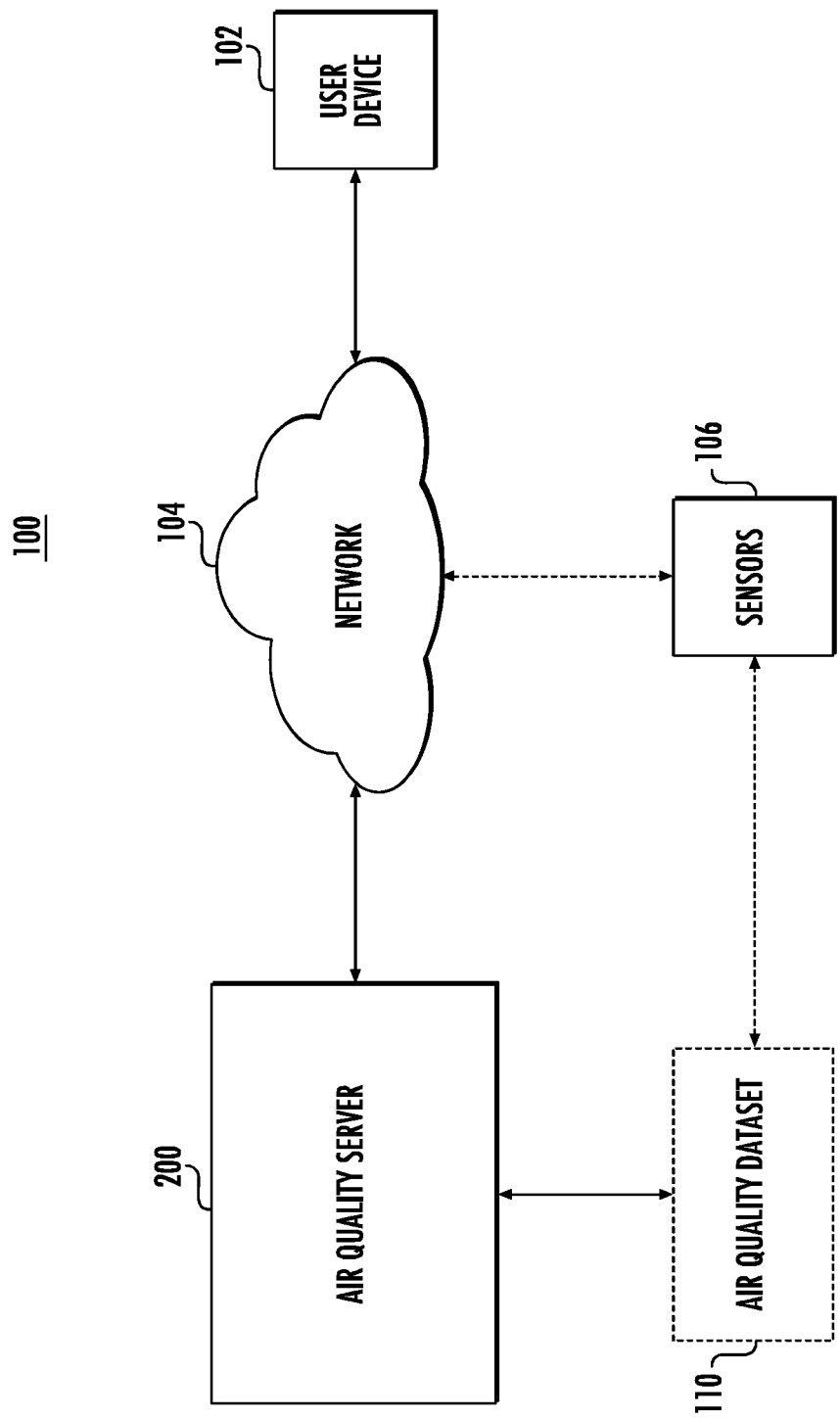
FIG. 1 illustrates a system diagram including devices that may be involved in some example embodiments described herein.

Some embodiments of the present invention will now be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout. As used herein, the description may refer to an air quality server as an example "apparatus." However, elements of the apparatus described herein may be equally applicable to the claimed method and computer program product. Thus, use of any such terms should not be taken to limit the spirit and scope of embodiments of the present invention.

Definition of Terms

As used herein, the terms "data," "content," "information," "electronic information," "signal," "command," and similar terms may be used interchangeably to refer to data capable of being transmitted, received, and/or stored in accordance with embodiments of the present disclosure. Thus, use of any such terms should not be taken to limit the spirit or scope of embodiments of the present disclosure. Further, where a first computing device is described herein to receive data from a second computing device, it will be appreciated that the data may be received directly from the second computing device or may be received indirectly via one or more intermediary computing devices, such as, for example, one or more servers, relays, routers, network access points, base stations, hosts, and/or the like, sometimes referred to herein as a "network." Similarly, where a first computing device is described herein as sending data to a second computing device, it will be appreciated that the data may be sent directly to the second computing device or may be sent indirectly via one or more intermediary computing devices, such as, for example, one or more servers, remote servers, cloud-based servers (e.g., cloud utilities), relays, routers, network access points, base stations, hosts, and/or the like.

As used herein, the term "comprising" means including but not limited to and should be interpreted in the manner it is typically used in the patent context. Use of broader terms such as comprises, includes, and having should be understood to provide support for narrower terms such as consisting of, consisting essentially of, and comprised substantially of.

As used herein, the phrases "in one embodiment," "according to one embodiment," "in some embodiments," and the like generally refer to the fact that the particular feature, structure, or characteristic following the phrase may be included in at least one embodiment of the present disclosure. Thus, the particular feature, structure, or characteristic may be included in more than one embodiment of the present disclosure such that these phrases do not necessarily refer to the same embodiment.

As used herein, the word "example" is used herein to mean "serving as an example, instance, or illustration." Any implementation described herein as "example" is not necessarily to be construed as preferred or advantageous over other implementations.

As used herein, the terms "user device," "mobile device," "electronic device" and the like refer to computer hardware that is configured (either physically or by the execution of software) to access one or more services made available by an air quality server (e.g., apparatus or computing device of the present disclosure) and, among various other functions, is configured to directly, or indirectly, transmit and receive data. Example user devices may include a smartphone, a tablet computer, a laptop computer, a wearable device (e.g., smart glasses, smart watch, or the like), and the like. In some embodiments, a user device may include a "smart device" that is equipped with a chip or other electronic device that is configured to communicate with the apparatus via Bluetooth, NFC, Wi-Fi, 3G, 4G, 5G, RFID protocols, and the like. By way of a particular example, a user device may be a mobile phone equipped with a Wi-Fi radio that is configured to communicate with a Wi-Fi access point that is in communication with the air quality server 200 or other computing device via a network.

As used herein, the term "sensor" or "sensors" refer to any object, device, or system which may be in network communication with the air quality server and/or the user device. The sensors may be configured to generate pollutant concentration data and iteratively transmit this data to the air quality server 200. For example, the sensors may refer to a nondispersive infra-red (NDIR) $CO_2$ sensor configured to determine the pollutant concentration of $CO_2$ proximate the sensors (e.g., in parts-per-million or the like).

As used herein, the term "air quality dataset" refers to a data structure or repository for storing sensor data, time data, pollutant concentration data, and the like. Similarly, the "pollutant concentration data" of the air quality dataset may refer to data generated by one or more sensors communicably coupled with the air quality server 200 and/or air quality dataset. The air quality dataset may be accessible by one or more software applications of the air quality server 200.

As used herein, the term "computer-readable medium" refers to non-transitory storage hardware, non-transitory storage device or non-transitory computer system memory that may be accessed by a controller, a microcontroller, a computational system or a module of a computational system to encode thereon computer-executable instructions or software programs. A non-transitory "computer-readable medium" may be accessed by a computational system or a module of a computational system to retrieve and/or execute the computer-executable instructions or software programs encoded on the medium. Exemplary non-transitory computer-readable media may include, but are not limited to, one or more types of hardware memory, non-transitory tangible media (for example, one or more magnetic storage disks, one or more optical disks, one or more USB flash drives), computer system memory or random access memory (such as, DRAM, SRAM, EDO RAM), and the like.

Having set forth a series of definitions called-upon throughout this application, an example system architecture and example apparatus is described below for implementing example embodiments and features of the present disclosure.

Device Architecture and Example Apparatus

With reference to FIG. 1, an example system 100 is illustrated with an apparatus (e.g., an air quality server 200)

communicably connected via a network 104 to a user device 102 and sensors 106. The example system 100 may also include an air quality dataset 110 that may be hosted by the air quality server 200 or otherwise hosted by devices in communication with the air quality server 200.

The air quality server 200 may include circuitry, networked processors, or the like configured to perform some or all of the apparatus-based (e.g., air quality server-based) processes described herein, and may be any suitable network server and/or other type of processing device. In this regard, air quality server 200 may be embodied by any of a variety of devices. For example, the air quality server 200 may be configured to receive/transmit data and may include any of a variety of fixed terminals, such as a server, desktop, or kiosk, or it may comprise any of a variety of mobile terminals, such as a portable digital assistant (PDA), mobile telephone, smartphone, laptop computer, tablet computer, or in some embodiments, a peripheral device that connects to one or more fixed or mobile terminals. Example embodiments contemplated herein may have various form factors and designs but will nevertheless include at least the components illustrated in FIG. 2 and described in connection therewith. In some embodiments, the air quality server 200 may be located remotely from the sensors 106, the user device 102, and/or air quality dataset 110, although in other embodiments, the air quality server 200 may comprise the sensors 106, the user device 102, and/or the air quality dataset 110. The air quality server 200 may, in some embodiments, comprise several servers or computing devices performing interconnected and/or distributed functions. Said differently, in some embodiments the air quality server 200 may be configured as a locally-hosted server, a cloud-based, distributed server, or a peer-to-peer network (e.g., user devices comprising the air quality server functionality). Despite the many arrangements contemplated herein, the air quality server 200 is shown and described herein as a single computing device to avoid unnecessarily overcomplicating the disclosure.

The network 104 may include one or more wired and/or wireless communication networks including, for example, a wired or wireless local area network (LAN), personal area network (PAN), metropolitan area network (MAN), wide area network (WAN), or the like, as well as any hardware, software and/or firmware for implementing the one or more networks (e.g., network routers, switches, hubs, etc.). For example, the network 104 may include a cellular telephone, mobile broadband, long term evolution (LTE), GSM/EDGE, UMTS/HSPA, IEEE 802.11, IEEE 802.16, IEEE 802.20, Wi-Fi, dial-up, and/or WiMAX network. Furthermore, the network 104 may include a public network, such as the Internet, a private network, such as an intranet, or combinations thereof, and may utilize a variety of networking protocols now available or later developed including, but not limited to TCP/IP based networking protocols.

The user device 102 may refer to a mobile device associated with a user and may be a cellular telephone (e.g., a smartphone and/or other type of mobile telephone), laptop, desktop, tablet, electronic reader, e-book device, media device, wearable, smart glasses, smartwatch, or any combination of the above. Although only a user device 102 is illustrated, the example system 100 may include any number of user devices associated with the same user or any number of respective other users. By way of example, in an instance in which the example system 100 operates as a peer-to-peer networking, the air quality server 200 may be in communication with a plurality of user devices.

As noted above, the sensors 106 may refer to any object, device, or system which may be in network communication with the air quality server and/or the user device and configured to generate pollutant concentration data. For example, the sensors may refer to a nondispersive infra-red (NDIR) $CO_2$ sensor configured to determine the pollutant concentration of $CO_2$ proximate the sensors (e.g., in parts-per-million or the like). While described herein with reference to $CO_2$ sensors, the present disclosure contemplates that any number of additional sensors may be used (e.g., pressure, temperature, or the like) and/or that the sensors 106 may be configured to, in addition to determining pollutant concentration, determine one or more additional operating parameters of the system 100. Furthermore, while described herein with reference to $CO_2$ as an example pollutant, the present disclosure contemplates that any other pollutant may be monitored and dissipated by the systems described herein.

The air quality dataset 110 may be stored by any suitable storage device configured to store some or all of the information described herein (e.g., memory 204 of the air quality server 200 or a separate memory system separate from the air quality server 200, such as one or more database systems, backend data servers, network databases, cloud storage devices, or the like provided by another device (e.g., online application or $3^{rd}$ party provider) or the user device 102). The air quality dataset 110 may comprise data received from the air quality server 200 (e.g., via a memory 204 and/or processor(s) 202), the sensors 106, or the user device 102, and the corresponding storage device may thus store this data.

Figure 2:
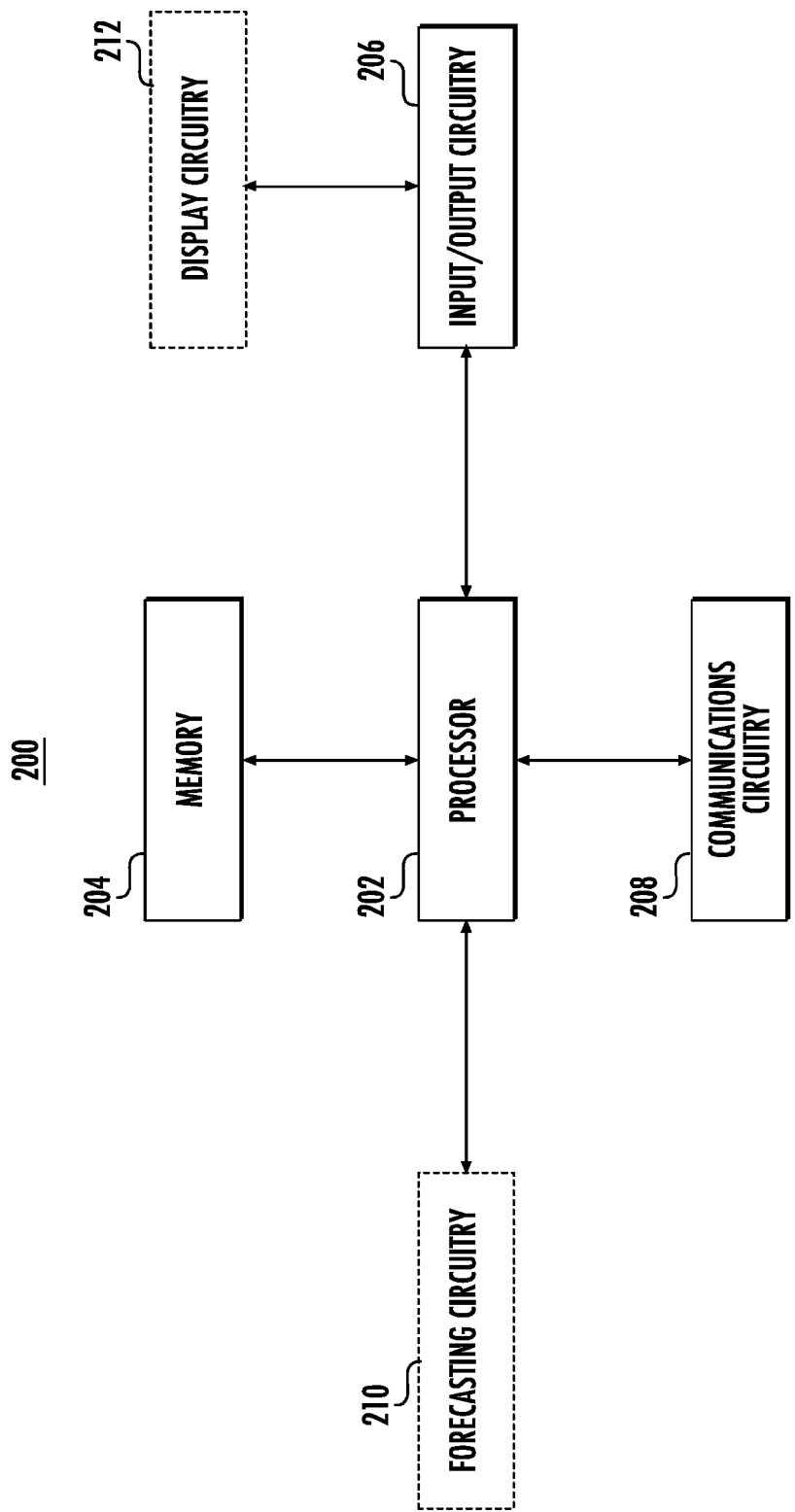
FIG. 2 illustrates a schematic block diagram of example circuitry that may perform various operations, in accordance with some example embodiments described herein.

As illustrated in FIG. 2, the air quality server 200 may include a processor 202, a memory 204, communications circuitry 208, input/output circuitry 206, and, in some embodiments, display circuitry 212 and forecasting circuitry 210. The air quality server 200 may be configured to execute the operations described below in connection with FIGS. 3-6. Although components 202-212 are described in some cases using functional language, it should be understood that the particular implementations necessarily include the use of particular hardware. It should also be understood that certain of these components 202-212 may include similar or common hardware. For example, two sets of circuitry may both leverage use of the same processor 202, memory 204, communications circuitry 208, or the like to perform their associated functions, such that duplicate hardware is not required for each set of circuitry. The use of the term "circuitry" as used herein includes particular hardware configured to perform the functions associated with respective circuitry described herein. As described in the example above, in some embodiments, various elements or components of the circuitry of the air quality server 200 may be housed within the sensors 106 and/or the user device 102. It will be understood in this regard that some of the components described in connection with the air quality server 200 may be housed within one of these devices, while other components are housed within another of these devices, or by yet another device not expressly illustrated in FIG. 1.

Of course, while the term "circuitry" should be understood broadly to include hardware, in some embodiments, the term "circuitry" may also include software for configuring the hardware. For example, although "circuitry" may include processing circuitry, storage media, network interfaces, input/output devices, and the like, other elements of the air quality server 200 may provide or supplement the functionality of particular circuitry.

In some embodiments, the processor 202 (and/or co-processor or any other processing circuitry assisting or otherwise associated with the processor) may be in communication with the memory 204 via a bus for passing information among components of the air quality server 200. The memory 204 may be non-transitory and may include, for example, one or more volatile and/or non-volatile memories. In other words, for example, the memory may be an electronic storage device (e.g., a non-transitory computer readable storage medium). The memory 204 may be configured to store information, data, content, applications, instructions, or the like, for enabling the air quality server 200 to carry out various functions in accordance with example embodiments of the present invention.

The processor 202 may be embodied in a number of different ways and may, for example, include one or more processing devices configured to perform independently. Additionally, or alternatively, the processor may include one or more processors configured in tandem via a bus to enable independent execution of instructions, pipelining, and/or multithreading. The use of the term "processing circuitry" may be understood to include a single core processor, a multi-core processor, multiple processors internal to the air quality server, and/or remote or "cloud" processors.

In an example embodiment, the processor 202 may be configured to execute instructions stored in the memory 204 or otherwise accessible to the processor 202. Alternatively, or additionally, the processor 202 may be configured to execute hard-coded functionality. As such, whether configured by hardware or by a combination of hardware with software, the processor 202 may represent an entity (e.g., physically embodied in circuitry) capable of performing operations according to an embodiment of the present invention while configured accordingly. Alternatively, as another example, when the processor 202 is embodied as an executor of software instructions, the instructions may specifically configure the processor 202 to perform the algorithms and/or operations described herein when the instructions are executed.

The air quality server 200 further includes input/output circuitry 206 that may, in turn, be in communication with processor 202 to provide output to a user and to receive input from a user, user device, or another source. In this regard, the input/output circuitry 206 may comprise display circuitry 212 that may be manipulated by a mobile application. In some embodiments, the input/output circuitry 206 may also include additional functionality such as a keyboard, a mouse, a joystick, a touch screen, touch areas, soft keys, a microphone, a speaker, or other input/output mechanisms. The processor 202 and/or user interface circuitry comprising the processor 202 may be configured to control one or more functions of a display through computer program instructions (e.g., software and/or firmware) stored on a memory accessible to the processor (e.g., memory 204, and/or the like).

The communications circuitry 208 may be any means such as a device or circuitry embodied in either hardware or a combination of hardware and software that is configured to receive and/or transmit data from/to a network and/or any other device, circuitry, or module in communication with the air quality server 200. In this regard, the communications circuitry 208 may include, for example, a network interface for enabling communications with a wired or wireless communication network. For example, the communications circuitry 208 may include one or more network interface cards, antennae, buses, switches, routers, modems, and supporting hardware and/or software, or any other device suitable for enabling communications via a network. Additionally, or alternatively, the communication interface may include the circuitry for interacting with the antenna(s) to cause transmission of signals via the antenna(s) or to handle receipt of signals received via the antenna(s). These signals may be transmitted by the air quality server 200 using any of a number of wireless personal area network (PAN) technologies, such as Bluetooth® v1.0 through v3.0, Bluetooth Low Energy (BLE), infrared wireless (e.g., IrDA), ultra-wideband (UWB), induction wireless transmission, or the like. In addition, it should be understood that these signals may be transmitted using Wi-Fi, Near Field Communications (NFC), Worldwide Interoperability for Microwave Access (WiMAX) or other proximity-based communications protocols.

The forecasting circuitry 210 includes hardware components designed to generate quality tendency projections, pollutant increase forecasts, and pollutant decrease forecasts. The forecasting circuitry 210 may utilize processing circuitry, such as the processor 202, to perform its corresponding operations, and may utilize memory 204 to store collected information. By way of example, in some instances, the forecasting circuitry 210 may query the air quality dataset 110 to receive pollutant concentration data.

In addition, computer program instructions and/or other type of code may be loaded onto a computer, processor or other programmable air quality server's circuitry to produce a machine, such that the computer, processor other programmable circuitry that execute the code on the machine create the means for implementing the various functions, including those described in connection with the components of air quality server 200.

As described above and as will be appreciated based on this disclosure, embodiments of the present invention may be configured as systems, methods, mobile devices, and the like. Accordingly, embodiments may comprise various means including entirely of hardware or any combination of software with hardware. Furthermore, embodiments may take the form of a computer program product comprising instructions stored on at least one non-transitory computer-readable storage medium (e.g., computer software stored on a hardware device). Any suitable computer-readable storage medium may be utilized including non-transitory hard disks, CD-ROMs, flash memory, optical storage devices, or magnetic storage devices.

Example Operations for Air Quality Maintenance

Figure 3:
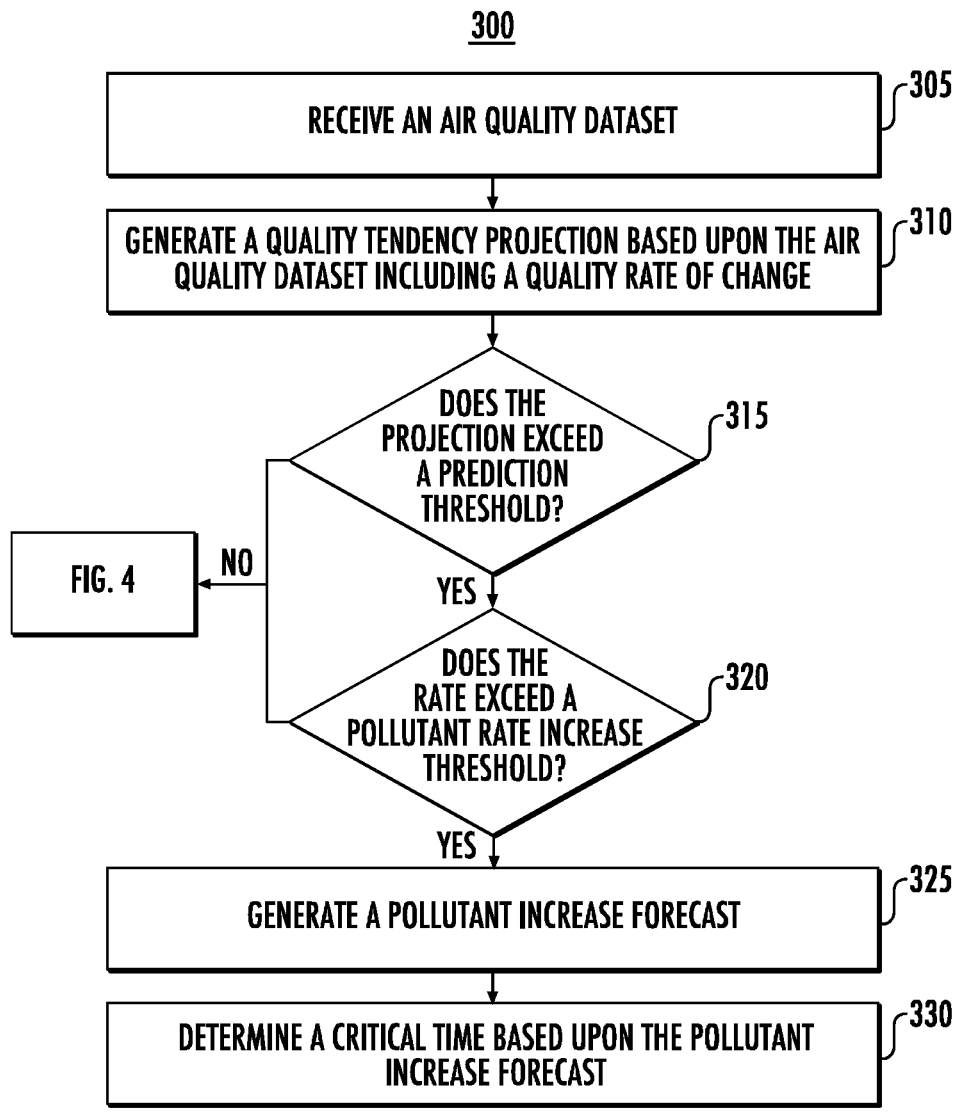
FIGS. 3-4 illustrate an example flowchart for air quality maintenance, in accordance with some example embodiments described herein.
Figure 4:
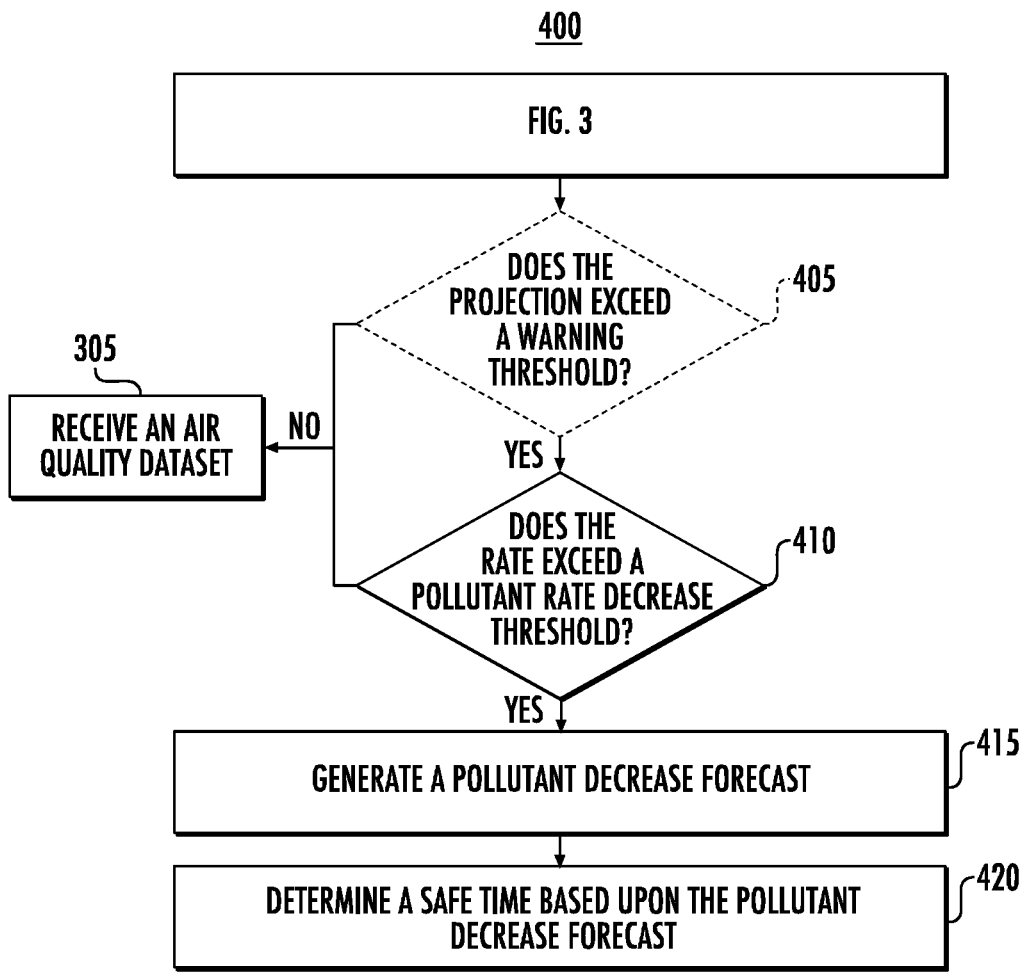

FIGS. 3-4 illustrate flowcharts containing a series of operations for performing air quality maintenance in accordance with some example embodiments described herein. The operations illustrated in FIGS. 3-4 may, for example, be performed by, with the assistance of, and/or under the control of an apparatus (e.g., air quality server 200), as described above. In this regard, performance of the operations may invoke one or more of processor 202, memory 204, input/output circuitry 206, communications circuitry 208, forecasting circuitry 210, and/or display circuitry 212.

As shown in operation 305, the apparatus (e.g., air quality server 200) includes means, such as input/output circuitry 206, communications circuitry 208, or the like, for receiving an air quality dataset. As described above, the air quality dataset 110 may be configured to store pollutant concentration data associated with respective time data as generated by the sensors 106. By way of example, the sensors 106 may be disposed within the interior of a building (e.g., a school) and may be configured to periodically (e.g., every two (2)

minutes) generate a pollutant concentration data entry with associated time data (e.g., time-stamped to indicate the time at which the pollutant concentration was determined). While described herein with reference to pollutant concentration data generated every two (2) minutes, the present disclosure contemplates that pollutant concentration data may be generate or received at any frequency.

In some embodiments, these pollutant concentration data entries may be transmitted directly to the air quality dataset 110 for storage. In other embodiments, the sensors 106 may transmit the pollutant concentration data to the air quality server 200 for performing one or more preprocessing steps, data smoothing, or related techniques on the pollutant concentration data. In such an embodiment, the air quality server 200 may subsequently transmit the pollutant concentration data to the air quality dataset 110 for storage. As such, receiving the air quality dataset at operation 305 may refer, in some embodiments, to pollutant concentration data received by the air quality server 200 directly from the sensors 106. In other embodiments, the air quality server 200 may query to air quality dataset 110 to retrieve the pollutant concentration data.

Thereafter, as shown in operation 310, the apparatus (e.g., air quality server 200) includes means, such as communications circuitry 208, forecasting circuitry 210, or the like, for generating a quality tendency projection based upon the air quality dataset including a quality rate of change. In generating the quality tendency projection, the air quality server 200 may analyze a plurality of pollutant concentration data received at operation 305 over a recent time period. As would be evident to one of ordinary skill in the art in light of the present disclosure, the recent time period (e.g., the amount of pollutant concentration data values analyzed) may be defined as any number of data points sufficient to generate a line as described hereafter. In particular, the forecasting circuitry 210 may analyze the plurality of pollutant concentration data entries and may utilize linear regression techniques, or by connecting end data points, generate a quality tendency projection in the form of a linear approximation. Furthermore, the quality tendency projection may be associated with a quality rate of change (e.g., the slope of the linear regression) that represents the rate of change of pollutant concentration (e.g., positive or negative). As described hereafter, a positive rate of change, in association with other threshold comparisons, may cause performance of an air degradation analysis procedure. A negative rate of change, in association with other threshold comparisons, may cause performance of a ventilation analysis procedure.

Thereafter, as shown in operations 315, 320 the apparatus (e.g., air quality server 200) includes means, such as processor 202, forecasting circuitry 210, or the like for comparing the quality tendency projection with a prediction threshold and comparing the quality rate of change with a pollutant rate increase threshold, respectively. As illustrated in the graphical representation of FIG. 7, the air quality server 200 may define various thresholds (e.g., associated with pollutant concentration) at which the air quality server 200 may initiate action. With reference to operation 315, the air quality server 200 may define, internally, via regulation, etc., a prediction threshold that corresponds to the pollutant concentration at which forecasting (e.g., a pollutant increase forecast) may occur. Similarly, with reference to operation 320, the quality rate of change refers to whether the pollutant concentration (e.g., the rate of change of the pollutant concentration) is increasing or decreasing.

By way of example, the air quality server 200 may generate a linear approximation (e.g., quality tendency projection) at operation 310 that, at a defined time, exceeds the prediction threshold (e.g., pollutant concentration is sufficiently high to begin remediation). In such an instance, the air quality server 200 may further compare the quality rate of change with a pollutant rate increase threshold at operation 320. Said differently, if the quality tendency projection indicates that the pollutant concentration is approaching concerning levels, the quality rate of change at operation 320 operates to determine if the pollutant concentration levels are decreasing such that no further increase forecasting is necessary (e.g., the pollutant concentration is not increasing). If either of the quality tendency projection or the quality rate of change fails to exceed the prediction threshold or pollutant rate increase threshold, respectively, the air quality server 200 may perform the operation associated with the ventilation analysis of FIG. 4 described hereafter.

Thereafter, as shown in operation 325, the apparatus (e.g., air quality server 200) includes means, such as the processor 202, the forecasting circuitry 210, or the like, for generating a pollutant increase forecast. As described hereafter with reference to FIG. 5, the forecasting circuitry 210 may analyze the air quality dataset received at operation 305, or a selected portion thereof, to select a parametric function that models the pollutant concentration data over the time period associated with the air quality dataset. By way of example, the forecasting circuitry 210 may model the pollutant concentration increase as a logarithmic curve, as an exponential curve, or the like based upon the pollutant concentration data. In some instances, generating the pollutant increase forecast may require optimization, data smoothing, etc. in order to select a function that properly models the forecast of future increase in pollutant concentration. By way of example, the forecasting circuitry 210 may identify and remove outlier pollutant concentration data entries (e.g., a sudden influx or reduction in an otherwise exponential increase in pollutant concentration).

Figure 7:
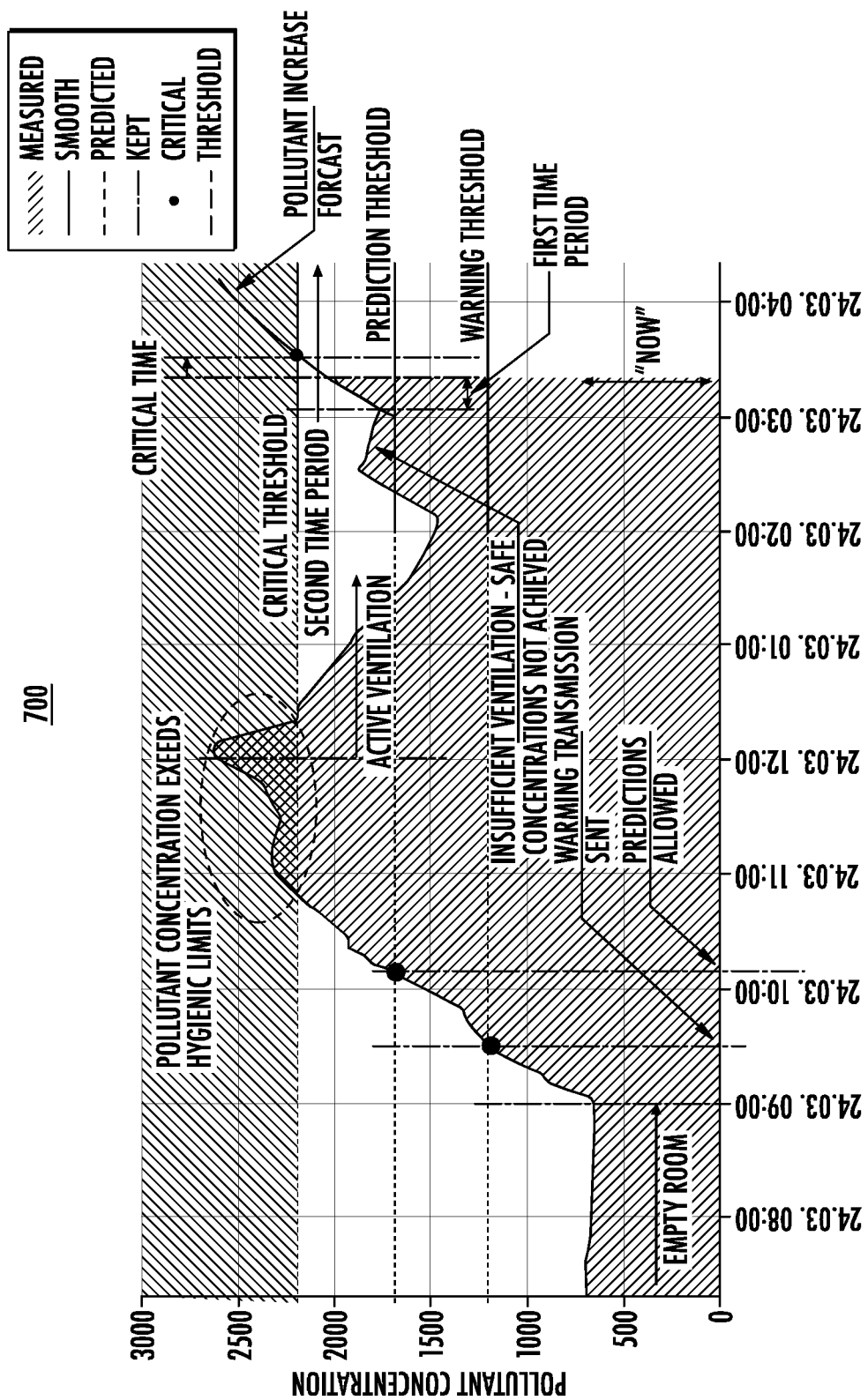
FIG. 7 illustrates a graphical representation of the air degradation analysis of FIG. 5, in accordance with some example embodiments described herein.

Thereafter, as shown in operation 330, the apparatus (e.g., air quality server 200) includes means, such as processor 202, forecasting circuitry 210, or the like for determining a critical time based upon the pollutant increase forecast. As described hereafter with reference to FIG. 5, the critical time comprises a time in which pollutant concentration is projected to exceed a critical threshold. As noted above, the air quality server 200 may define various thresholds (e.g., associated with pollutant concentration) at which the air quality server 200 may initiate action. A critical threshold may be defined internally by the air quality server 200, by associated air quality regulations, or the like, and may refer to a pollutant concentration level above which pollutant concentration exceeds hygienic/safe limits. In order to determine the critical time at which the pollutant concentration is projected to exceed the critical threshold, the forecasting circuitry 210 may be configured to extend (e.g. forecast) the selected parametric function described above over a future time period (e.g., a second time period in FIG. 5) to generate the pollutant increase forecast. Said differently, the system may extend the selected parametric function domain to such time in the future that the function intersects with the critical threshold as illustrated in FIG. 7.

Turning next to FIG. 4, a flowchart is shown for performing a ventilation analysis 400 of the air quality maintenance method of FIG. 3. The operations illustrated in FIG. 4 may, for example, be performed by, with the assistance of, and/or under the control of an apparatus (e.g., air quality server 200), as described above. In this regard, performance of the operations may invoke one or more of processor 202, memory 204, input/output circuitry 206, communications circuitry 208, forecasting circuitry 210, and/or display circuitry 212.

As shown in operation 405, the apparatus (e.g., air quality server 200) includes means, such as input/output circuitry 206, communications circuitry 208, forecasting circuitry 210, or the like, for comparing the quality tendency projection with a warning threshold and comparing the quality rate of change with a pollutant rate decrease threshold, respectively. As illustrated in the graphical representation of FIG. 8, the air quality server 200 may define various thresholds (e.g., associated with pollutant concentration) at which the air quality server 200 may initiate action. With reference to operation 405, the air quality server 200 may define, internally, via regulation, etc., a warning threshold that corresponds to the pollutant concentration at which initial concern may occur (e.g., and associated initial warnings provided to a user device 102). As is evident by the ventilation analysis hereafter, the pollutant concentration must exceed the warning threshold at operation 405 for ventilation to occur (e.g., a request for ventilation). Said differently, if the pollutant concentration fails to exceed the warning concentration, no ventilation may be necessary. Similarly, with reference to operation 410, the quality rate of change refers to whether the pollutant concentration (e.g., the rate of change of the pollutant concentration) is increasing or decreasing.

By way of example, the air quality server 200 may generate a linear approximation (e.g., quality tendency projection) at operation 310 of FIG. 3 that, at a defined time, exceeds the warning threshold (e.g., pollutant concentration is worthy of consideration). In such an instance, the air quality server 200 may further compare the quality rate of change with a pollutant rate decrease threshold at operation 410 (e.g., given that the operations of FIG. 3 indicate that the pollutant concentration is not increasing). Said differently, if the quality tendency projection indicates that the pollutant concentration exceeds the warning threshold, but the quality rate of change at operation 410 indicates that the pollutant concentration levels are decreasing, the ventilation analysis described hereafter may be used to estimate the time required to reach a safe pollutant concentration. If either of the quality tendency projection or the quality rate of change fails to exceed the prediction threshold or pollutant rate decrease threshold, respectively, the air quality server 200 may iteratively receive an air quality dataset as described above with reference to operation 305 (e.g., no further analysis is necessary). Although described herein with reference to exceeding a warning threshold at operation 405, the present disclosure contemplates that, in some embodiments, the ventilation analysis described herein may occur in instances in which the projection does not exceed the warning threshold.

Thereafter, as shown in operation 415, the apparatus (e.g., air quality server 200) includes means, such as the processor 202, the forecasting circuitry 210, or the like, for generating a pollutant decrease forecast in instances in which the quality tendency projection and the quality rate of change exceed the warning threshold and the pollutant rate decrease threshold, respectively. As described hereafter with reference to FIG. 6, the forecasting circuitry 210 may analyze the air quality dataset received at operation 305, or a selected portion thereof, to select a parametric function that models the pollutant concentration data over the time period associated with the air quality dataset. By way of example, the forecasting circuitry 210 may model the pollutant concentration decrease as a rational function, as an exponential curve, or the like based upon the pollutant concentration data. In some instances, generating the pollutant decrease forecast may require optimization, data smoothing, etc. in order to select a function that properly models the forecast of future decrease in pollutant concentration. By way of example, the forecasting circuitry 210 may identify and remove outlier pollutant concentration data entries (e.g., a sudden influx or reduction in an otherwise exponential increase in pollutant concentration).

Figure 8:
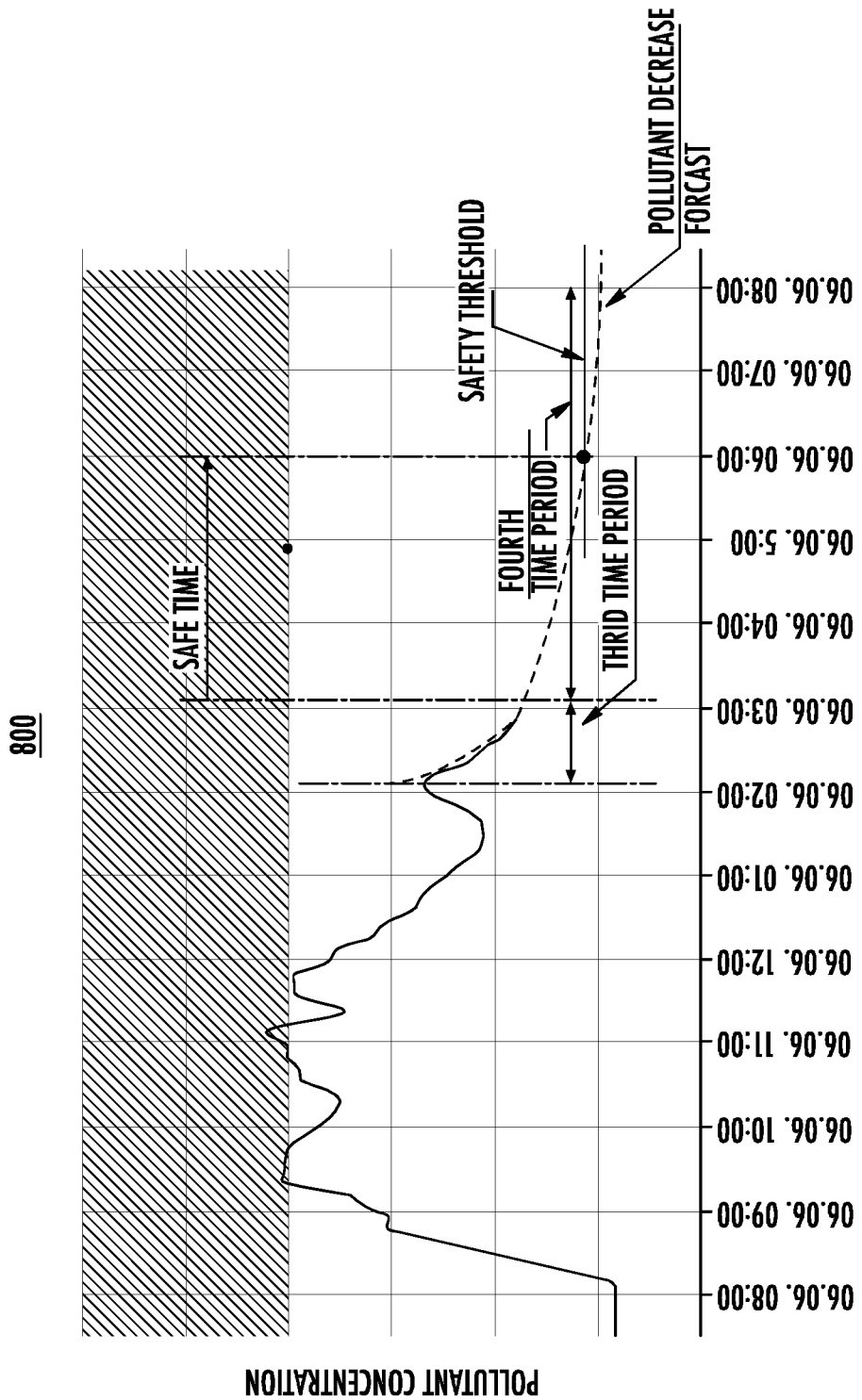
FIG. 8 illustrates a graphical representation of the ventilation analysis of FIG. 6, in accordance with some example embodiments described herein.

Thereafter, as shown in operation 420, the apparatus (e.g., air quality server 200) includes means, such as processor 202, forecasting circuitry 210, or the like for determining a safe time based upon the pollutant decrease forecast. As described hereafter with reference to FIG. 6, the safe time comprises a time in which the pollutant concentration is projected to satisfy a safety threshold. A safety threshold may be defined internally by the air quality server 200, by associated air quality regulations, or the like, and may refer to a pollutant concentration level below which pollutant concentration is safe for human interaction. In order to determine the safe time at which the pollutant concentration is projected to satisfy the safety threshold, the forecasting circuitry 210 may be configured to extend (e.g. forecast) the selected parametric function described at operation 415 over a future time period (e.g., fourth time period in FIG. 6) to generate the pollutant decrease forecast. Said differently, the system may extend the selected parametric function domain to such time in the future that the function intersects with the safety threshold as illustrated in FIG. 8.

In some embodiments, the warning threshold described above with reference to operation 405 may further operate to generate a warning transmission for sending to the user device 102. For example, in some instances, the quality tendency projection generated at operation 310 may extend (e.g., even if decreasing) to exceed the warning threshold. As such, the air quality server 200, via the communication circuitry 208 of the like, may generate a warning transmission and transmit said transmission to the user device 102. In other instances, the air quality dataset received at operation 305 may include at least one pollutant concentration data entry that exceeds the warning threshold. In such an instance, the air quality server 200 may similarly generate a warning transmission and transmit said transmission to the user device 102.

Figure 5:
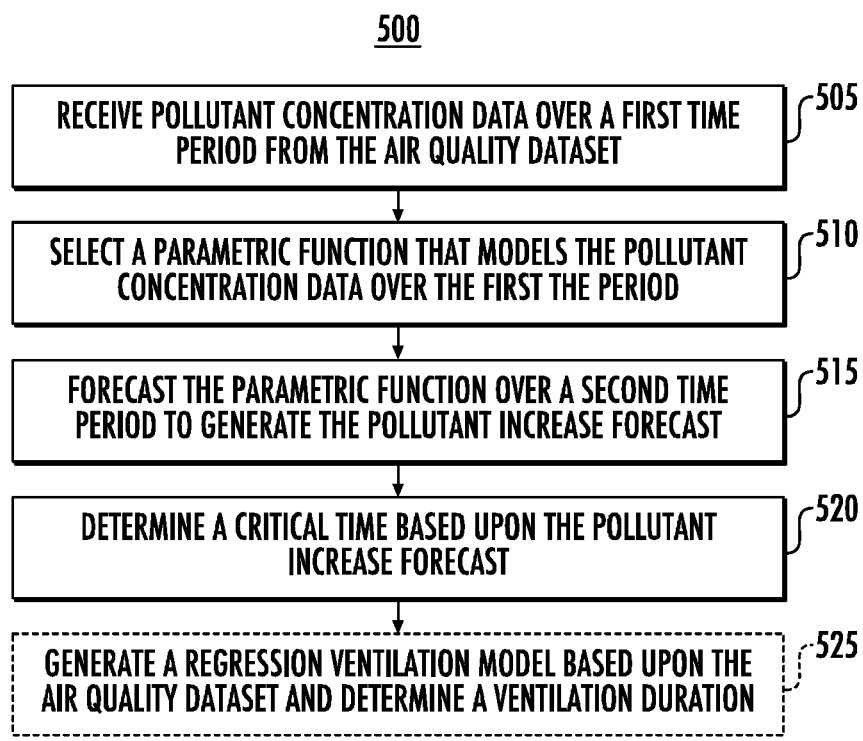
FIG. 5 illustrates an example flowchart for air degradation analysis, in accordance with some example embodiments described herein.

Turning next to FIG. 5, a flowchart is shown for performing air degradation analysis. The operations illustrated in FIG. 5 may, for example, be performed by, with the assistance of, and/or under the control of an apparatus (e.g., air quality server 200), as described above. In this regard, performance of the operations may invoke one or more of processor 202, memory 204, input/output circuitry 206, communications circuitry 208, forecasting circuitry 210, and/or display circuitry 212.

As shown in operation 505, the apparatus (e.g., air quality server 200) includes means, such as input/output circuitry 206, communications circuitry 208, or the like, for receiving pollutant concentration data over a first time period from the air quality dataset. As described above, the air quality dataset 110 may be configured to store pollutant concentration data associated with respective time data as generated by the sensors 106. As such, the communications circuitry 208 may be configured to query the air quality dataset 110 to retrieve the pollutant concentration data. In particular, the air quality server 200 may be configured to receive air quality data with associated time data indicative of the first time period (e.g., pollutant concentration data from the previous hour). As would be evident to one of ordinary skill in the art in light of the present disclosure, the first time period may refer to any previous-in-time period during which pollutant concentration data was generated. Furthermore, in some embodiments, the air quality server 200 may employ one or more machine learning or other trainable model to iteratively improve the determination of the first time period.

Thereafter, as shown in operation 510, the apparatus (e.g., air quality server 200) includes means, such as processor 202, forecasting circuitry 210, or the like for selecting a parametric function that models the pollutant concentration data over the first time period. By way of example, the forecasting circuitry 210 may model the pollutant concentration increase as a logarithmic curve ($f(t)=p_0+p_1 \cdot \ln(p2 \cdot ts+1)$), as an exponential curve ($f(t)=p_0+p_1 \cdot e^{-p_2 \cdot t}$), or the like based upon the pollutant concentration data. In some instances, generating the pollutant increase forecast may require optimization, data smoothing, etc. in order to select a function that properly models the forecast of future increase in pollutant concentration as described above. In light of the potential variability of the first time period described with reference to operation 505, the parametric function selected to model the pollutant concentration data may iteratively change based upon the selection of the first time period.

Thereafter, as shown in operation 515, the apparatus (e.g., air quality server 200) includes means, such as processor 202, forecasting circuitry 210, or the like for forecasting the parametric function over a second time period to generate the pollutant increase forecast. The forecasting circuitry 210 may be configured to extend (e.g. forecast) the selected parametric function over a future time period (e.g., second time period) to generate the pollutant increase forecast. Said differently, the system may extend the selected parametric function domain to such time in the future (e.g., the second time period) that the function intersects with the critical threshold as illustrated in FIG. 7. As such, as shown in operation 520, the apparatus (e.g., air quality server 200) includes means, such as processor 202, forecasting circuitry 210, or the like for determining a critical time based upon the pollutant increase forecast. As described above, the critical time comprises a time in which pollutant concentration is projected to exceed a critical threshold. The critical threshold may be defined internally by the air quality server 200, by associated air quality regulations, or the like, and may refer to a pollutant concentration level above which pollutant concentration exceeds hygienic/safe limits. The critical time may therefore be as the time at which the forecasted parametric function intersects with the critical threshold.

In some embodiments, as shown in operation 525, the apparatus (e.g., air quality server 200) includes means, such as processor 202, forecasting circuitry 210, or the like for generating a regression ventilation model based upon the air quality dataset and determine a ventilation duration. As would be evident to one of ordinary skill in the art in light of the present disclosure, once a critical time is determined, the air quality server 200 may operate to reduce the pollutant concentration by ventilating air as described hereafter with reference to FIG. 6. In some embodiments, the forecasting circuitry 210 may generate a regression ventilation model based upon the air quality dataset and determine a ventilation duration based upon the regression ventilation model. The ventilation duration may comprise a time required to reduce the pollutant concentration to satisfy the safety threshold as described hereafter. Said differently, once a critical pollutant concentration is reached, the regression ventilation model may operate similar to method 600 (e.g., forecasting a parametric function to generate the pollutant decrease forecast).

Inn some embodiments, however, the air quality server 200 may not receive current in time data sufficient to initially generate the regression ventilation model, such as instances in which the room has yet to be ventilated. As such, the forecasting circuitry 210 may query the air quality dataset 110 for historical ventilation data. In such an embodiment, the air quality server 200 may operate in concurrence with a historical ventilation model (e.g., a pollutant decrease forecast) to initially reduce the pollutant concentration. Upon a sufficient ventilation time during which the sensors 106, the air quality server 200, etc. are monitoring the pollutant concentration and iteratively adjusting the venting procedure (e.g., adjusting airflow or the like), the air quality server 200 may be trained to generate the regression ventilation model based on current pollutant concentration data (e.g., may use a training model to estimate the safe time based on current data).

Figure 6:
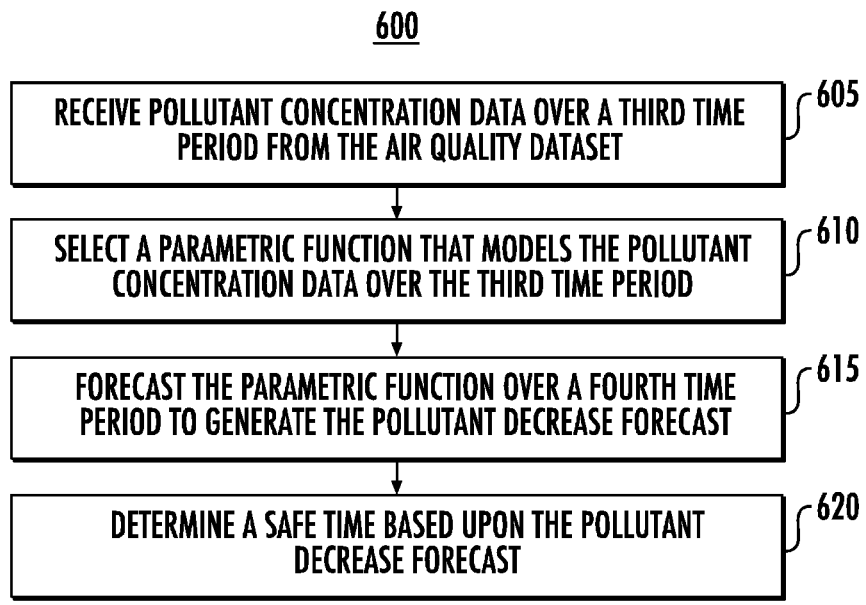
FIG. 6 illustrates an example flowchart for ventilation analysis, in accordance with some example embodiments described herein.

Turning next to FIG. 6, a flowchart is shown for performing ventilation analysis. The operations illustrated in FIG. 6 may, for example, be performed by, with the assistance of, and/or under the control of an apparatus (e.g., air quality server 200), as described above. In this regard, performance of the operations may invoke one or more of processor 202, memory 204, input/output circuitry 206, communications circuitry 208, forecasting circuitry 210, and/or display circuitry 212.

Similar to the air degradation analysis of FIG. 5, as shown in operation 605, the apparatus (e.g., air quality server 200) includes means, such as input/output circuitry 206, communications circuitry 208, or the like, for receiving pollutant concentration data over a third time period from the air quality dataset. As described above, the air quality dataset 110 may be configured to store pollutant concentration data associated with respective time data as generated by the sensors 106. As such, the communications circuitry 208 may be configured to query the air quality dataset 110 to retrieve the pollutant concentration data. In particular, the air quality server 200 may be configured to receive air quality data with associated time data indicative of the third time period (e.g., pollutant concentration data from the previous hour). As would be evident to one of ordinary skill in the art in light of the present disclosure, the third time period may also refer to any previous-in-time period during which pollutant concentration data was generated, and may, in some instances correspond to the first time period. Furthermore, in some embodiments, the air quality server 200 may employ one or more machine learning or other trainable model to iteratively improve the determination of the third time period (e.g., improve identifying sufficient pollutant data for the operations herein).

Thereafter, as shown in operation 610, the apparatus (e.g., air quality server 200) includes means, such as processor 202, forecasting circuitry 210, or the like for selecting a parametric function that models the pollutant concentration data over the third time period. By way of example, the forecasting circuitry 210 may model the pollutant concentration decrease as an exponential curve ($f(t)=p_0+p_1 \cdot e^{-p_2 \cdot t}$), a rational function ($f(t)=p_0+p_1/(t-p_2)$), or the like based upon the pollutant concentration data. In some instances, generating the pollutant decrease forecast may require optimization, data smoothing, etc. in order to select a function that properly models the forecast of future decrease in pollutant concentration as described above. In light of the potential variability of the third time period described with reference to operation 605, the parametric function selected to model the pollutant concentration data may iteratively change based upon the selection of the first time period.

Thereafter, as shown in operation 615, the apparatus (e.g., air quality server 200) includes means, such as processor 202, forecasting circuitry 210, or the like for forecasting the parametric function over a fourth time period to generate the pollutant decrease forecast. The forecasting circuitry 210 may be configured to extend (e.g. forecast) the selected parametric function over a future time period (e.g., fourth time period) to generate the pollutant decrease forecast. Said differently, the system may extend the selected parametric function domain to such time in the future (e.g., the fourth time period) that the function intersects with the safety threshold as illustrated in FIG. 8. As such, as shown in operation 620, the apparatus (e.g., air quality server 200) includes means, such as processor 202, forecasting circuitry 210, or the like for determining a safe time based upon the pollutant decrease forecast. As described above, the safe time comprises a time in which pollutant concentration is projected to satisfy a safety threshold. The safety threshold may be defined internally by the air quality server 200, by associated air quality regulations, or the like, and may refer to a pollutant concentration level below which pollutant concentration is safe for human interaction. The safety time may therefore be defined as the time at which the forecasted parametric function intersects with the safety threshold.

FIGS. 3-6 thus illustrate flowcharts describing the operation of apparatuses, methods, and computer program products according to example embodiments contemplated herein. It will be understood that each flowchart block, and combinations of flowchart blocks, may be implemented by various means, such as hardware, firmware, processor, circuitry, and/or other devices associated with execution of software including one or more computer program instructions. For example, one or more of the operations described above may be implemented by an apparatus executing computer program instructions. In this regard, the computer program instructions may be stored by a memory 204 of the air quality server 200 and executed by a processor 202 of the air quality server 200. As will be appreciated, any such computer program instructions may be loaded onto a computer or other programmable apparatus (e.g., hardware) to produce a machine, such that the resulting computer or other programmable apparatus implements the functions specified in the flowchart blocks. These computer program instructions may also be stored in a computer-readable memory that may direct a computer or other programmable apparatus to function in a particular manner, such that the instructions stored in the computer-readable memory produce an article of manufacture, the execution of which implements the functions specified in the flowchart blocks. The computer program instructions may also be loaded onto a computer or other programmable apparatus to cause a series of operations to be performed on the computer or other programmable apparatus to produce a computer-implemented process such that the instructions executed on the computer or other programmable apparatus provide operations for implementing the functions specified in the flowchart blocks.

The flowchart blocks support combinations of means for performing the specified functions and combinations of operations for performing the specified functions. It will be understood that one or more blocks of the flowcharts, and combinations of blocks in the flowcharts, can be implemented by special purpose hardware-based computer systems which perform the specified functions, or combinations of special purpose hardware with computer instructions.

With reference to FIGS. 7-8, graphical representations of the air degradation analysis of FIG. 5, and the ventilation analysis of FIG. 6 are illustrated, respectively. Pollutant concentration over a period of time is shown with pollutant concentration varying in response to the methods described herein. As shown, the air quality server 200 may define a critical threshold that, with respect to pollutant concentration, is greater than the prediction threshold. Similarly, the prediction threshold may be defined as greater than the warning threshold. Furthermore, as illustrated in FIG. 8, the warning threshold may be greater than the safety threshold.

CONCLUSION

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

What is claimed is:

1. A computer-implemented method for performing air quality maintenance, the computer-implemented method comprising:
receiving an air quality dataset associated with an environment, wherein the air quality dataset comprises pollutant concentration data associated with respective time data;
generating a quality tendency projection based upon the air quality dataset, wherein the quality tendency projection comprises a quality rate of change;
in an instance in which the quality tendency projection exceeds a prediction threshold and the quality rate of change exceeds a pollutant rate increase threshold, performing air degradation analysis comprising:
generating a pollutant increase forecast; and
determining a critical time based upon the pollutant increase forecast, wherein the critical time comprises a time in which pollutant concentration is projected to exceed a critical threshold; and
in an instance in which the quality rate of change exceeds a pollutant rate decrease threshold, performing ventilation analysis comprising:
generating a pollutant decrease forecast; and
determining a safe time based upon the pollutant decrease forecast, wherein the safe time comprises a time in which the pollutant concentration is projected to satisfy a safety threshold; and
automatically causing ventilating of air from the environment based at least in part on the safe time, wherein ventilating the air reduces a concentration of a pollutant in the environment.

2. The computer-implemented method according to claim 1, further comprising, in an instance in which the quality tendency projection exceeds a warning threshold;
generating a warning transmission; and
transmitting the warning transmission to a user device disposed within the environment.

3. The computer-implemented method according to claim 1, further comprising, in an instance in which at least one pollutant concentration data entry exceeds a warning threshold;
generating a warning transmission; and
transmitting the warning transmission to a user device disposed within the environment.

4. The computer-implemented method according to claim 1, wherein performing the degradation analysis further comprises:
receiving pollutant concentration data over a first time period from the air quality dataset;
selecting a parametric function that models the pollutant concentration data over the first time period; and
forecasting the parametric function over a second time period to generate the pollutant increase forecast.

5. The computer-implemented method according to claim 1, wherein performing the ventilation analysis further comprises:
receiving pollutant concentration data over a third time period from the air quality dataset;
selecting a parametric function that models the pollutant concentration data over the third time period; and
forecasting the parametric function over a fourth time period to generate the pollutant decrease forecast.

6. The computer-implemented method according to claim 1, in response to determining the critical time, further comprising:
generating a regression ventilation model based upon the air quality dataset; and
determining a ventilation duration based upon the regression ventilation model, wherein the ventilation duration comprises a time required to reduce the pollutant concentration to satisfy the safety threshold.

7. The computer-implemented method according to claim 1, wherein:
the critical threshold is greater the prediction threshold;
the prediction threshold is greater than a warning threshold; and
the warning threshold is greater than the safety threshold.

8. The computer-implemented method according to claim 1, further comprising:
generating the air quality dataset based at least in part on the pollutant concentration data generated via at least one sensor in the environment.

9. The computer-implemented method according to claim 1, further comprising:
generating at least a portion of the pollutant concentration data within the environment generated by each sensor of a plurality of sensors in the environment.

10. The computer-implemented method according to claim 1, wherein receiving an air quality dataset associated with an environment comprises:
receiving at least a portion of the air quality dataset directly from at least one sensor in the environment.

11. The computer-implemented method according to claim 1, wherein the pollution concentration data is received via at least one sensor in the environment comprising at least a first sensor of a user device in the environment.

12. The computer-implemented method according to claim 1, wherein each step is performed by at least one computing device of a system communicatively coupled with at least one sensor in the environment, and wherein the pollutant concentration data is generated via at least one sensor in the environment.

13. An apparatus configured to perform air quality maintenance, the apparatus comprising:
at least one processor and at least one non-transitory memory including program code, the at least one non-transitory memory and the program code configured to, with the processor, cause the apparatus to at least:
receive an air quality dataset associated with an environment, wherein the air quality dataset comprises pollutant concentration data associated with respective time data;
generate a quality tendency projection based upon the air quality dataset, wherein the quality tendency projection comprises a quality rate of change;
in an instance in which the quality tendency projection exceeds a prediction threshold and the quality rate of change exceeds a pollutant rate increase threshold, perform air degradation analysis to:
generate a pollutant increase forecast; and
determine a critical time based upon the pollutant increase forecast, wherein the critical time comprises a time in which pollutant concentration is projected to exceed a critical threshold; and
in an instance in which the quality rate of change exceeds a pollutant rate decrease threshold, perform ventilation analysis to:
generate a pollutant decrease forecast; and
determine a safe time based upon the pollutant decrease forecast, wherein the safe time comprises a time in which the pollutant concentration is projected to satisfy a safety threshold; and
automatically cause ventilating of air from the environment based at least in part on the safe time, wherein the ventilating of the air reduces a concentration of a pollutant in the environment.

14. The apparatus according to claim 13, wherein the memory including the program code is further configured to, with the processor, cause the apparatus to, in an instance in which the quality tendency projection exceeds a warning threshold;
generate a warning transmission; and
transmit the warning transmission to a user device disposed within the environment.

15. The apparatus according to claim 13, wherein the memory including the program code is further configured to, with the processor, cause the apparatus to, in an instance in which at least one pollutant concentration data entry exceeds a warning threshold;
generate a warning transmission; and
transmit the warning transmission to a user device disposed within the environment.

16. The apparatus according to claim 13, wherein the memory including the program code is further configured to, with the processor, cause the apparatus to:
receive pollutant concentration data over a third time period from the air quality dataset;
select a parametric function that models the pollutant concentration data over the third time period; and
forecast the parametric function over a fourth time period to generate the pollutant decrease forecast.

17. The apparatus according to claim 13, wherein the memory including the program code is further configured to, with the processor, cause the apparatus to:

generate a regression ventilation model based upon the air quality dataset; and determine a ventilation duration based upon the regression ventilation model, wherein the ventilation duration comprises a time required to reduce the pollutant concentration to satisfy the safety threshold.

18. A computer program product comprising at least one non-transitory computer-readable storage medium having computer-readable program code portions stored therein, the computer-readable program code portions comprising an executable portion configured to:

receive an air quality dataset associated with an environment, wherein the air quality dataset comprises pollutant concentration data associated with respective time data;

generate a quality tendency projection based upon the air quality dataset, wherein the quality tendency projection comprises a quality rate of change;

in an instance in which the quality tendency projection exceeds a prediction threshold and the quality rate of change exceeds a pollutant rate increase threshold, perform air degradation analysis to:

generate a pollutant increase forecast; and determine a critical time based upon the pollutant increase forecast, wherein the critical time comprises a time in which pollutant concentration is projected to exceed a critical threshold; and in an instance in which the quality rate of change exceeds a pollutant rate decrease threshold, perform ventilation analysis to:

generate a pollutant decrease forecast; and determine a safe time based upon the pollutant decrease forecast, wherein the safe time comprises a time in which the pollutant concentration is projected to satisfy a safety threshold; and automatically cause ventilating of air from the environment based at least in part on the safe time, wherein the ventilating of the air reduces a concentration of a pollutant in the environment.

19. The computer program product according to claim 18, wherein the computer-readable program code portions comprising the executable portion are configured to, in an instance in which the quality tendency projection exceeds a warning threshold:

generate a warning transmission; and transmit the warning transmission to a user device disposed within the environment.

20. The computer program product according to claim 18, wherein the computer-readable program code portions comprising the executable portion are further configured to, in an instance in which at least one pollutant concentration data entry exceeds a warning threshold;

generate a warning transmission; and transmit the warning transmission to a user device disposed within the environment.

* * * * *